United States Patent [19]

Lee

[11] 4,036,962

[45] July 19, 1977

[54] 6,7-METHYLENEDIOXY-1-(2,2,2-TRI-FLUOROETHYL)-4(1H)-QUINOLONE-3-CARBOXYLIC ACID AND ITS SALTS AND ESTERS

[75] Inventor: Kyu Tai Lee, Wilmington, Del.

[73] Assignee: E. I. Du Pont de Nemours and Co., Wilmington, Del.

[21] Appl. No.: 578,137

[22] Filed: May 16, 1975

Related U.S. Application Data

[63] Continuation-in-part of Ser. No. 496,851, Aug. 12, 1974, abandoned.

[51] Int. Cl.$^2$ ............................................. C07D 215/56
[52] U.S. Cl. ............................... 424/258; 260/287 AN
[58] Field of Search ................. 424/258; 260/287 AN

[56] References Cited

U.S. PATENT DOCUMENTS

| 3,496,184 | 2/1970 | Mizzoni et al. | 260/287 AN |
| 3,591,697 | 7/1971 | Kaminsky et al. | 260/287 AN |
| 3,725,413 | 4/1973 | Genzer et al. | 260/287 AN |
| 3,865,832 | 2/1975 | Boschman et al. | 260/287 AN |

OTHER PUBLICATIONS

Burger, "Medicinal Chemistry", 1970, 3rd Ed., pp. 72 and 760, (for footnote).

*Primary Examiner*—Donald G. Daus
*Assistant Examiner*—David E. Wheeler

[57] ABSTRACT

Certain novel 6,7-methylenedioxy-1-(2,2,2-trifluoroethyl)-4(1H)-quinolone-3-carboxylic acid esters are useful in the treatment of bacterial infections in warm-blooded animals. The novel 6,7-methylenedioxy-1-(2,2,2-trifluoroethyl)-4(1H)-quinolone-3-carboxylic acid and its salts and alkyl esters of 1 to 3 carbon atoms are useful as chemical intermediates.

6 Claims, No Drawings

6,7-METHYLENEDIOXY-1-(2,2,2-TRIFLUOROETHYL)-4(1H)-QUINOLONE-3-CARBOXYLIC ACID AND ITS SALTS AND ESTERS

CROSS-REFERENCE TO RELATED APPLICATION

This application is a continuation-in-part of my copending application Ser. No. 496,851, filed Aug. 12, 1974 now abandoned.

BACKGROUND OF THE INVENTION

This invention relates to novel 6,7-methylenedioxy-1-(2,2,2-trifluoroethyl)-4(1H)-quinolone-3-carboxylic acid esters and their use in the treatment of bacterial infections in warm-blooded animals. The novel free acid 6,7-methylenedioxy-1-(2,2,2-trifluoroethyl)-4(1H)-quinolone-3-carboxylic acid and its salts and alkyl esters of 1 to 3 carbon atoms are useful chemical intermediates.

U.S. Pat. No. 3,287,458 (to Kaminsky) discloses novel antibacterial 1,4-dihydro-1-lower alkyl-6,7-methylenedioxy-4-oxo-3-quinoline-carboxylic acids of the formula:

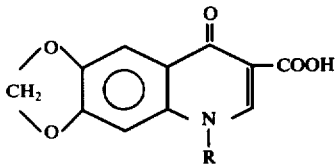

wherein R is lower alkyl such as methyl, ethyl, propyl, isopropyl, butyl, isobutyl, or cycloalkyl such as cyclopropyl, cyclobutyl, cyclohexyl, or lower alkenyl such as allyl or vinyl and to the alkali metal salts thereof. R may also be a substituted lower alkyl such as hydroxy lower alkyl or carboxy lower alkyl or aralkyl, such as phenyl lower alkyl in which lower alkyl has the same meaning as defined.

The acid compound of the present invention differs structurally from that of U.S. Pat. No. 3,287,458 having an ethyl radical in the 1-position in that three fluorine atoms replace the hydrogen on the 2-carbon atom of the ethyl group. The 1-ethyl compound of U.S. Pat. No. 3,287,458 is known as oxolinic acid and will be referred to as such hereafter.

There is a need for new antibacterial agents as strains of bacteria can develop which are more resistant or immune to the antibacterial agents in use.

SUMMARY OF THE INVENTION

The invention comprises certain novel 6,7-methylenedioxy-1-(2,2,2-trifluoroethyl)-4(1H)-quinolone-3-carboxylic acid esters useful in the treatment of bacterial infections. These compounds are of the formula

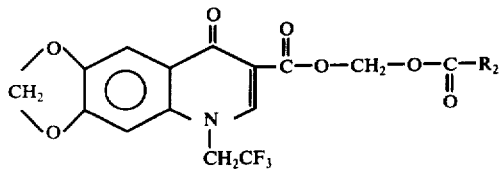

wherein
R$_2$ is selected from the group consisting of primary, secondary, or tertiaryalkyl radicals of 1 to 10 carbon atoms, cycloalkyl radicals from 3 to 10 carbon atoms, and phenyl.

Preferred are the compounds wherein R$_2$ is tertiary alkyl, especially tertiary butyl.

The above compounds can be formulated as pharmaceutical compositions comprising a pharmaceutical carrier and a compound of the above formula.

The invention also comprises the novel 6,7-methylenedioxy-1-(2,2,2-trifluoroethyl)-4(1H)-quinolone-3-carboxylic acid and its salts and alkyl esters of 1 to 3 carbon atoms. These compounds are useful chemical intermediates and are of the formula:

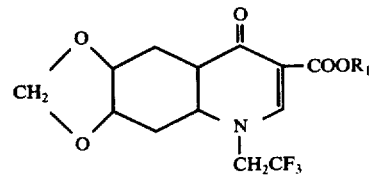

Compound I wherein
R$_1$ is selected from the group consisting of hydrogen, a univalent cation selected from Na$^+$, K$^+$, NH$_4^+$, Li$^+$, ½ Ca$^{++}$, ½ Mg$^{++}$, and alkyl of 1 to 3 carbon atoms.

DETAILED DESCRIPTION OF THE INVENTION

The suitable pharmaceutical compositions containing one or more of the ester compounds of this invention exhibit potent antibacterial activity, particularly against such gram-negative bacteria as the Escherichia group and Proteus group. In addition, the compounds have also exhibited a high antibacterial activity against such gram-positive bacteria as the Staphylococci and Bacillus groups. This, combined with their low order of toxicity, provides useful therapeutic agents for the treatment of infections caused by susceptible organisms in warm-blooded animals including man.

In a systemic *Escherichia coli* infection of mice at two infecting levels of bacteria a preferred compound of this invention, 6,7-methylenedioxy-1-(2,2,2-trifluoroethyl)-4(1H)-quinolone-3-carboxylic acid, trimethylacetoxymethyl ester shows significantly greater antibacterial activity than does oxolinic acid.

The synthesis of compound I wherein R$_1$ is hydrogen starts with the reaction between 3,4-methylenedioxyaniline and the 2,2,2-trifluoroethyl ester of trichloromethane-sulfonic acid (J. Med. Chem., 16, 1360 (1973)) in the presence of an acid-scavenger such as triethylamine or pyridine. The reaction is carried out in an inert solvent such as toluene or benzene at elevated temperature of 50° to 200° C., preferably 80°–130° C. The resulting trifluoroethylaniline is isolated in pure form by distillation.

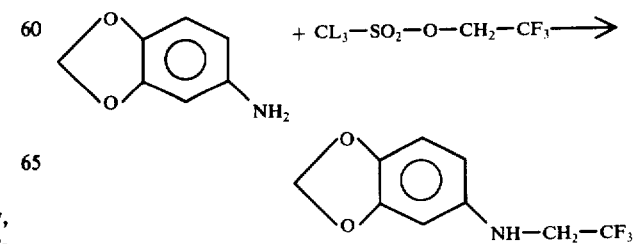

The above trifluoroethylaniline is then reacted with diethyl ethoxymethylenemalonate at 100°-200° C., preferably 140°-150° C. for 1-10 hours. The resulting adduct, diethyl[3,4-methylenedioxy-N-(2,2,2-trifluoroethyl)]anilinomethylenemalonate, is usually a viscous oil, but pure enough to be used for the next reaction without further purification.

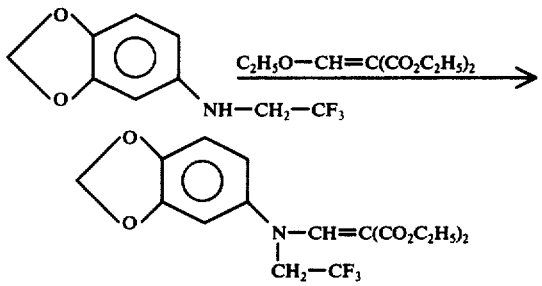

The ring closure of the above resulting malonate adduct is accomplished by mixing it in polyphosphoric acid and heating at 100°-140° C., usually 115°-120° C. for between 20 and 60 minutes. The mixture is diluted with ice water and the solid product, 6,7-methylenedioxy-1-(2,2,2-trifluoroethyl)-4(1H)-quinolone-3-carboxylic acid, ethyl ester, is isolated.

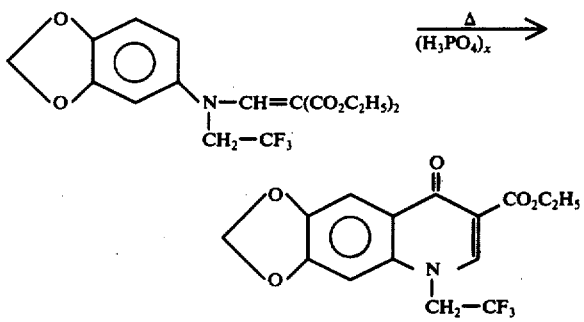

The ring closure is also feasible by treating the above malonate adduct with phosphorous oxychloride, or phosphorous pentachloride in nitrobenzene, or with boron trifluoride etherate, or polyphosphate ester.

The ethyl ester is hydrolyzed in aqueous acid such as 6-N hydrochloric acid of 6-N sulfuric acid at elevated temperature. The reaction is usually over in 1 to 5 hours to give the product 6,7-methylenedioxy-1-(2,2,2-trifluoroethyl)-4(1H)-quinolone-3-carboxylic acid.

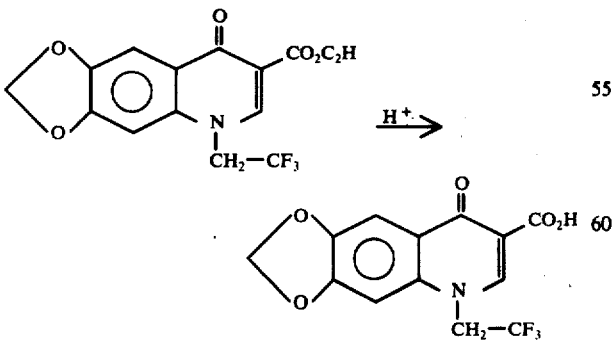

An alternate method of synthesis of 6,7-methylenedioxy-1-(2,2,2-trifluoroethyl)-4(1H)-quinolone-3-carboxylic acid involves the trifluoro-ethylation of 1,4-dihydro-6,7-methylenedioxy-4-oxo-3-carboxylic acid, ethyl ester (J. Med. Chem. 11, 160 (1968)) with the 2,2,2-trifluoroethyl ester of trichloromethanesulfonic acid. A strong base such as sodium hydride or potassium tertiary butoxide is used to generate anion and the reaction is carried out in an inert polar solvent, preferably dimethyl formamide or dimethyl sulfoxide. The ethyl ester derived is again hydrolyzed to give the final product.

The desired esters are prepared by reacting the 6,7-methylenedioxy-1-(2,2,2-trifluoroethyl)-4(1H)-quinolone-3-carboxylic acid with chloromethyl ester of an appropriate carboxylic acid, such as chloromethyl trimethylacetate, in the presence of a base, such as triethylamine or potassium carbonate. Suitable solvents for this reaction are dimethyl formamide or dimethyl sulfoxide.

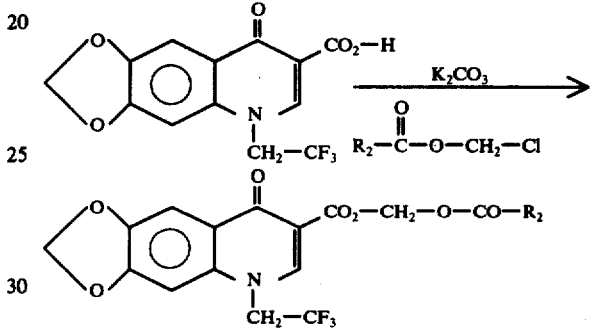

In the following examples, references to temperature will be in degrees centigrade.

EXAMPLE 1

3,4-Methylenedioxy-N-(2,2,2-trifluoroethyl)aniline

A mixture of 7 g. (0.051 mole) of 3,4-methylenedioxyaniline, 14.5 g. (0.051 mole) 2,2,2-trifluoroethyl trichloromethanesulfonate, and 5.2 g. (0.052 mole) of triethylamine in 60 ml. of toluene was heated under reflux for 3¼ hours. The cooled mixture was washed with water, dried over anhydrous magnesium sulfate, and concentrated under reduced pressure. The oily residue is distilled (b.p. 1.9 mm. 103°-5°) to give pure 3,4-methylenedioxy-N-(2,2,2-trifluoroethyl)aniline.

EXAMPLE 2

Diethyl [3,4-methylenedioxy-N-(2,2,2-trifluoroethyl)-]anilinomethylene malonate

A mixture of 18 g. (0.0823 mole) of the aniline obtained from Example 1 and 17.8 g. (0.0823 mole) of diethyl ethoxymethylenemalonate was heated to 140°-150° C. until the evolution of ethanol ceases (about 3-4 hours). The viscous oily product is pure enough to be used without further purification.

EXAMPLE 3

6,7-Methylenedioxy-1-(2,2,2-trifluoroethyl)-4(1H)-quinolone-3-carboxylic acid, ethyl ester A mixture of 10 g. of the malonate obtained from Example 2 and 50 g. of polyphosphoric acid was heated at 115°-120° C. for 25 minutes with stirring. The mixture was then poured into 500 ml. of ice water. The pH was adjusted to about 2 by adding 50% sodium hydroxide solution and the solid was collected by filtration. The solid, the acid ester, was recrystallized from ethyl acetate-diethyl ether mixture and then with ethanol, m.p.: 204°–6° C.

Anal. calc'd. for $C_{15}H_{12}F_3NO_5$; C, 52.48; H, 3.52; N, 4.08. Found: C, 52.47; H, 3.68; N, 4.18.

EXAMPLE 4

6,7-Methylenedioxy-1-(2,2,2-trifluoroethyl)-4(1H)-quinolone-3-carboxylic acid

A mixture of 1 g. of the ethyl ester obtained from Example 3 and 40 ml. of 6N. hydrochloric acid was heated under reflux for 1½ hours. The mixture was cooled and the solid product was collected by filtration and washed with water and dried under reduced pressure, m.p. 323°–5° C (dec.).

Anal. calc'd. for $C_{13}H_8F_3NO_5$; C, 49.54; H, 2.56; N, 4.45. Found C, 49.44; H, 2.58; N, 4.49.

EXAMPLE 5

6,7-Methylenedioxy-1-(2,2,2-trifluoroethyl)-4(1H)-quinolone-3-carboxylic acid

A mixture of 15.6 (0.06 mole) of 6,7-methylenedioxy-4(1H)-quinolone-3-carboxylic acid, ethyl ester (J. Med. Chem. 11, 160 (1968)) and 1.5 g. (0.062 mole) of sodium hydride powder in 250 ml. of dimethyl formamide was heated with stirring for 0.5 hour at 80°–90° C. 2,2,2-Trifluoroethyl trichloromethanesulfonate (17.5 g. 0.62 mole) was then added dropwise. The temperature is maintained at 80°–90° for an additional 2 hours. The cooled mixture was poured into ice water and the solid product was isolated by filtration. It was recrystallized from ethanol. This product was identical to that obtained from Example 4.

EXAMPLE 6

6,7-Methylenedioxy-1-(2,2,2-trifluoroethyl)-4(1H)-quinolone-3-carboxylic acid, trimethylacetoxymethyl ester To a mixture of 2.6 g. 6,7-methylenedioxy-1-(2,2,2-trifluoroethyl)-4(1H)-quinolone-3-carboxylic acid and 35 ml. of dimethyl formamide was added 1.4 g. of triethylamine. The mixture was warmed to 55° and kept there for ½ hour. 2.8 g. of chloromethyl trimethylacetate was then added and the resulting mixture was stirred at 55° for 5 hours. The cooled solution was diluted with 150 ml. of ethyl acetate and washed with water. The ethyl acetate solution was dried over magnesium sulfate and concentrated. The solid residue, 6,7-methylenedioxy-1-(2,2,2-trifluoroethyl)-4(1H)-quinolone-3-carboxylic acid, trimethylacetoxymethyl ester, was recrystallized from $CH_2Cl_2$-ether mixture; m.p. 190°–1°.

Anal. Calc'd. for $C_{19}H_{18}F_3NO_7$: C, 53.15; H, 4.23; N, 3.26. Found C, 53.14; H, 4.20; N, 3.24.

The ester thus obtained was found to be the metastable crystalline form. Thus, when this compound was recrystallized from high boiling solvent such as acetonitrile or ethyl acetate, or when it was left at room temperature for a long time, a different crystalline ester (more stable) was obtained: m.p. 199°–200°.

Anal. Calc'd. for $C_{19}H_{18}F_3NO_7$: C, 53.15; H, 4.23; N, 3.26. Found C, 53.55; H, 4.38; N, 3.52.

The nmr spectra of the two esters are identical. Biologically, the stable form was found to be less active than the meta-stable, probably due to poor absorption.

The procedure of Example 6 can be repeated using the indicated "chloromethyl ester" in place of the chloromethyl trimethylacetate of Example 6 to obtain the indicated "products."

|     | chloromethyl ester              | Products                                                                                                                              |
| --- | ------------------------------- | ------------------------------------------------------------------------------------------------------------------------------------- |
| 6A. | chloromethyl iso-butyrate       | 6,7-methylenedioxy-1-(2,2,2-trifluoroethyl)-4(1H)-quinolone-3-carboxylic acid, iso-butyryloxymethyl ester m.p. 169–171°                |
| 6B. | chloromethyl 2,2-dimethyl-n-butyrate | 6,7-methylenedioxy-1-(2,2,2-trifluoroethyl)-4(1H)-quinolone-3-carboxylic acid, 2,2-dimethyl-n-butyryloxymethyl ester, m.p. 169–170° |
| 6C. | chloromethyl n-hexanoate        | 6,7-methylenedioxy-1-(2,2,2-trifluoroethyl)-4(1H)-quinolone-3-carboxylic acid, n-hexanoyloxymethyl ester, m.p. 113–5°                  |
| 6D. | chloromethyl n-decanoate        | 6,7-methylenedioxy-1-(2,2,2-trifluoroethyl)-4(1H)-quinolone-3-carboxylic acid, n-decanoyloxymethyl ester, m.p. 119–120°                |
| 6E. | chloromethyl cyclohexane-carboxylate | 6,7-methylenedioxy-1-(2,2,2-trifluoroethyl)-4(1H)-quinolone-3-carboxylic acid, cyclohexanecarbonyloxymethyl ester, m.p. 176–8°    |
| 6F. | chloromethyl benzoate           | 6,7-methylenedioxy-1-(2,2,2-trifluoroethyl)-4(1H)-quinolone-3-carboxylic acid, benzoyloxymethyl ester, m.p. 192–4°                     |

EXAMPLE 7

The salts of 6,7-methylenedioxy-1-(2,2,2-trifluoroethyl)-4(1H)-quinolone-3-carboxylic acid are prepared by mixing a dimethyl formamide solution of the acid with equivalent amount of aqueous base (ammonium hydroxide or other alkaline hydroxide). The resulting mixture is then diluted with ethanol and the solid salts are isolated by filtration. This reaction is reversible, therefore, the acid can be obtained from the salt.

EXAMPLE 8

To a mixture of 2.6 g. of 6,7-methylenedioxy-1-(2,2,2-trifluoroethyl)-4(1H)-quinolone-3-carboxylic acid and 35 ml. of dimethyl formamide was added 1.4 g. of potassium carbonate. The mixture was stirred at room temperature for ½ hr. and 3 g. of chloromethyl trimethylacetate was added. The resulting mixture was stirred at room temperature for 3 days and poured into 200 ml. of water. The solid precipitate was collected by filtration and dissolved in $CH_2Cl_2$. The $CH_2Cl_2$ solution was dried over anhydrous magnesium sulfate and concentrated to give a solid product, which is identical to that obtained in Example 6.

EXAMPLE A

Use of the ester of this invention as antibacterial agents is exemplified by data for 6,7-methylene-1-(2,2,2-trifluoroethyl)-4(1H)-quinolone-3-carboxylic acid, trimethylacetoxymethyl ester. In vivo determinations of antibacterial activity are carried out in mice.

The test bacterium is grown into bacteriological medium from frozen stock cultures. The culture is centrifuged, resuspended, centrifuged again, resuspended in fresh bacteriological medium, and diluted to the proper infective concentration. Mice are infected by intraperitoneal or intravenous injection of 0.2 ml. of the diluted bacterial culture.

Test compounds are dissolved or suspended in water containing 0.01% Tween 80 by either sonication or bead-milling to break up the materials in order to dissolve them or provide a fine suspension for the insoluble compounds. Concentrations are prepared so that when 0.2 ml. of the solution or suspension is administered to mice orally by intubation, the correct amount of compound in mg/kg of mouse is provided.

The mice are dosed with test compound orally by intubation at appropriate intervals following infection and mortality is recorded through the third day. The effective dose 50 ($ED_{50}$) and lethal dose for 50% kill ($LD_{50}$) are calculated by the Reed-Muench method.

In Table I are the results of a test in mice infected with *Escherichia coli* by the intraperitoneal route. Compound was administered orally by intubation immediately following infection and again 4 hours after infection.

In a similar manner the effective doses of other compounds prepared as shown in Examples 6A to 6F are shown in Table II.

The determination of the dosage to be prescribed to combat a bacterial infection in a particular warm-blooded animal is within the capability of a person of ordinary skill in the art. For example, for mice, 10 to 400 mg/kg per is the recommended dosage to combat the infection with 100 to 200 mg/kg being preferred. For man, 5 to 100 mg/kg per day is the dosage to combat the infection with 5 to 10 mg/kg being preferred.

Besides the active ingredient, the pharmaceutical dosage form will contain a solid, semi-solid, or liquid pharmaceutical carrier, and may also contain other additives such as lubricants, binding agents, wetting agents, disintegrants, preservatives, colorants, and flavors which are common to the art.

In one type of the pharmaceutical compositions of this invention, the carrier is a capsule which can be of the ordinary gelatin type. In the capsules will be from about 5 to 90% by weight of a compound of the invention and 95% to 10% of a carrier. In another embodiment, the active ingredient is tableted with suitable diluent. These tablets will generally constitute from 1% to about 90% and preferably from 5% to 90% by weight of active ingredient. These dosage forms can contain from about 5 to about 500 milligrams of active ingredient, with about 20 to 250 preferred.

The pharmaceutical carrier can be a sterile liquid such as water or an oil, including those of petroleum, animal, vegetable oils of synthetic origin, for example peanut oil, soybean oil, mineral oil, sesame oil, and the like. In general, water, saline, aqueous dextrose (glucose) and related sugar solutions and glycols such as propylene glycol or polyethylene glycols are preferred liquid carriers, particularly for injectable solutions. Sterile injectable solutions such as saline will ordinarily contain from about 0.5% to 25% and preferably about 1 to 10% by weight of the active ingredient.

Liquid oral administration can be in a suitable suspen-

TABLE 1

COMPARISONS OF OXOLINIC
ACID AND 6,7-METHYLENEDIOXY-1-(2,2,2-TRIFLUOROETHYL)-
4(1H)-QUINOLONE-3-CARBOXYLIC ACID TRIMETHYLACETOXYMETHYL
ESTER AT TWO E. COLI MOUSE INFECTION LEVELS

| Compound | Mg/Kg[1] PO | 135 $LD_{50}$[2] % Survivors | $ED_{50}$ Mg/Kg | 18 $LD_{50}$[2] % Survivors | $ED_{50}$ Mg/Kg |
|---|---|---|---|---|---|
| 6,7-Methylenedixoy-1-(2,2,2-trifluoroethyl)-4(1H)-quinolone-3-carboxylic acid trimethyl-acetoxymethyl ester | 10 | 17 | 77 | 33 | 24 |
|  | 30 | 8 |  | 50 |  |
|  | 100 | 50 |  | 75 |  |
| Oxolinic Acid | 10 | 17 | >100 | 8 | 45 |
|  | 30 | 17 |  | 33 |  |
|  | 100 | 25 |  | 83 |  |
| Control |  | 14 |  | 14 |  |

[1]Animals dosed orally at the time of infection and again four hours later
[2]Determined by agar plate counts and stock culture titration, the dose is the $LD_{50}$ multiplied by the number preceding it.

TABLE 2

The $ED_{50}$ Values of Other Esters on E. coli infected mice

| Compounds | 2 $LD_{50}$ $ED_{50}$ (mg./kg.) | 4 $LD_{50}$ $ED_{50}$ (mg./kg.) |
|---|---|---|
| 6A |  | 73 |
| 6B |  | 40 |
| 6C |  | 25 |
| 6D | 19 |  |
| 6E | 29 |  |
| 6F |  | 34 |

The compounds of this invention may be employed as pharmaceutical compositions in such formulations such as injectables; oral forms such as tablets, hard gelatin capsules, solt gelatin capsules, suspensions, syrups, and elixirs; topicals such as ointments and lotions; nasal drops or ointments; rectal suppositories or foams; and vaginal suppositories or foam; and solutions may be sprayed for inhalation therapy. The active ingredient will be present in the amount of at least 0.5% by weight based on the total weight of the composition and not more than 90% by weight.

sion syrup or elixir, in which the active ingredient ordinarily will constitute from about 0.5 to 20% and preferably about 1 to 10% by weight. The pharmaceutical carrier in such composition can be a watery vehicle such as an aromatic water, a syrup, a pharmaceutical mucilage, or a hydro-alcoholic elixir.

Suitable pharmaceutical carriers, diluents, and additives are described in "Remington's Pharmaceutical Sciences" by E. W. Martin, a well-known reference text in this field.

The following examples will further illustrate the preparation of pharmaceutical compositions of the invention.

EXAMPLE I

A large number of unit capsules are prepared by filling standard two-piece hard gelatin capsules each with 100 milligrams of the compound of Example 6, 200 milligrams of lactose, 50 milligrams of starch, 30 milligrams of talc, and 10 milligrams of magnesium stearate.

EXAMPLE II

A mixture of the compound of Example 6 in soybean oil is prepared and placed in soft gelatin capsules containing 100 milligrams of the active ingredient.

Example III

A large number of tablets are prepared by conventional procedures so that the dosage unit is 250 milligrams of the compound of Example 6, 50 milligrams of microcrystalline cellulose, 40 milligrams of starch, 5 milligrams polyvinyl pyrrolidone, 155 milligrams lactose, 5 milligrams magnesium stearate. Appropriate coatings may be applied to increase palatability or delay absorption.

EXAMPLE IV

A parentral composition suitable for administration by injection is prepared by conventional procedures. This preparation contains 5% by weight of the compound of Example 6 in 10% by volume propylene glycol and water, and 0.9% benzyl alcohol.

EXAMPLE V

A suppository dosage form contains 7.5% of the compound of Example 6 and 95% by weight of theobroma oil.

EXAMPLE VI

An aqueous suspension is prepared for oral administration so that each 5 milliliters contain 100 milligrams of the finely divided compound of Example 6, 500 milligrams of acacia, 5 milligrams of sodium benzoate, 1.0 grams of sorbitol solution, U.S.P., 5 milligrams of sodium saccharin, and 0.025 milliliters of vanilla tincture.

I claim:
1. A compound of the formula

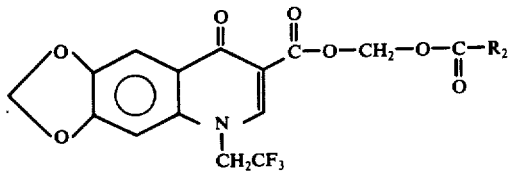

wherein $R_2$ is tertiary alkyl of 4–10 carbon atoms wherein the carbon adjacent to the carbonyl is the tertiary carbon.

2. The compound of claim 1 which is 6,7-methylenedioxy-1-(2,2,2-trifluoroethyl)-4(1H)-quinolone-3-carboxylic acid, trimethylacetoxymethyl ester.

3. A method of treating bacterial infection in a warm-blooded animal which comprises administering to the warm-blooded animal an effective antibacterial amount of a compound of claim 1.

4. A method of treating bacterial infection in a warm-blooded animal which comprises administering to the warm-blooded animal an effective antibacterial amount of a compound of claim 2.

5. A pharmaceutical composition comprising a suitable pharmaceutical carrier and an effective antibacterial amount of a compound of claim 1.

6. A pharmaceutical composition comprising a suitable pharmaceutical carrier and an effective antibacterial amount of a compound of claim 2.

* * * * *